United States Patent
Oz et al.

(10) Patent No.: US 9,713,430 B2
(45) Date of Patent: Jul. 25, 2017

(54) ACOUSTIC SENSORS FOR ABDOMINAL FETAL CARDIAC ACTIVITY DETECTION

(71) Applicant: Nuvo Group Ltd., Tel Aviv (IL)

(72) Inventors: Oren Oz, Modiin (IL); Ilya Divinsky, Tel Aviv (IL); Nathan Intrator, Tel Aviv (IL)

(73) Assignee: Nuvo Group Ltd., Ramat Gan (IL)

( * ) Notice: Subject to any disclaimer, the term of this patent is extended or adjusted under 35 U.S.C. 154(b) by 0 days.

(21) Appl. No.: 15/071,884

(22) Filed: Mar. 16, 2016

(65) Prior Publication Data

US 2016/0270685 A1 Sep. 22, 2016

Related U.S. Application Data

(63) Continuation-in-part of application No. 14/921,489, filed on Oct. 23, 2015, now Pat. No. 9,392,952.

(60) Provisional application No. 62/133,485, filed on Mar. 16, 2015.

(51) Int. Cl.

| A61B 5/0444 | (2006.01) |
|---|---|
| A61B 7/02 | (2006.01) |
| A61B 5/024 | (2006.01) |
| A61B 5/0245 | (2006.01) |
| A61B 5/0402 | (2006.01) |
| A61B 5/04 | (2006.01) |
| A61B 5/00 | (2006.01) |
| A61B 5/0452 | (2006.01) |
| A61B 5/0456 | (2006.01) |

(52) U.S. Cl.
CPC .......... *A61B 5/0444* (2013.01); *A61B 7/02* (2013.01); *A61B 5/0245* (2013.01); *A61B 5/02405* (2013.01); *A61B 5/02411* (2013.01); *A61B 5/0402* (2013.01); *A61B 5/04014* (2013.01); *A61B 5/04017* (2013.01); *A61B 5/0456* (2013.01); *A61B 5/04525* (2013.01); *A61B 5/4362* (2013.01); *A61B 5/6823* (2013.01); *A61B 5/6833* (2013.01); *A61B 5/7203* (2013.01); *A61B 2503/02* (2013.01); *A61B 2562/0204* (2013.01)

(58) Field of Classification Search
CPC ..... A61B 5/0444; A61B 7/02; A61B 5/02411; A61B 5/0245; A61B 5/6804; A61B 5/0402; A61B 5/04017; A61B 5/4362; A61B 5/04525; A61B 5/7203
See application file for complete search history.

(56) References Cited

U.S. PATENT DOCUMENTS

| 6,171,263 | B1 * | 1/2001 | Sullivan | A61B 5/02411 600/500 |
|---|---|---|---|---|
| 6,766,145 | B2 | 7/2004 | Fitzgerald et al. | |
| 7,818,050 | B2 | 10/2010 | Rapoport et al. | |
| 8,884,832 | B2 | 11/2014 | Huang et al. | |
| 2005/0277841 | A1 * | 12/2005 | Shennib | A61B 5/0444 600/511 |

(Continued)

OTHER PUBLICATIONS

PCT International Search Report and Written Opinion for PCT Application No. PCT/IB16/00454, dated Aug. 12, 2016.

*Primary Examiner* — Catherine Voorhees
(74) *Attorney, Agent, or Firm* — Greenberg Traurig LLP

(57) ABSTRACT

The invention provides systems and methods for monitoring the wellbeing of a fetus by the non-invasive detection and analysis of fetal cardiac activity data.

9 Claims, 11 Drawing Sheets

(56) References Cited

U.S. PATENT DOCUMENTS

2007/0219480 A1* 9/2007 Kamen ................ G05D 7/0647
604/20
2014/0205374 A1 7/2014 Nias et al.
2016/0262687 A1* 9/2016 Vaidyanathan ...... A61B 5/7264

* cited by examiner

ACOUSTIC SENSORS FOR ABDOMINAL FETAL CARDIAC ACTIVITY DETECTION

CROSS REFERENCE TO RELATED APPLICATIONS

This application claims priority to U.S. Provisional Patent Application No. 62/133,485, filed on Mar. 16, 2015, and U.S. patent application Ser. No. 14/921,489, filed on Oct. 23, 2015, the entire contents of which are incorporated by reference in their entirety.

FIELD OF THE INVENTION

The invention relates generally to acoustic sensors suitable for use in fetal heart rate monitoring systems.

BACKGROUND

Monitoring fetal cardiac can be useful to determine of the health of a fetus during pregnancy.

SUMMARY

In one embodiment, the present invention provides an acoustic sensor configured to detect fetal cardiac activity signals, comprising:
a) a body formed of a solid integral mass having a circular apron with two opposite major side walls,
   i. one side wall being concave in configuration and the other side wall having a rearwardly facing portion coaxially formed thereon, the rearwardly facing portion defining an attachment for a microphone;
   ii. an opening coaxially formed through the rearwardly facing portion; and
   iii. an annular edge connecting the periphery of the side walls;
b) a microphone, attached to the rearwardly facing portion,
   wherein the microphone is configured to produce electrical signals in response to acoustic signals transmitted from an abdomen of a pregnant subject;
c) a flexible membrane covering the one side wall,
   wherein the edge of the flexible membrane covers the annular edge of the one side wall,
   wherein the flexible membrane is configured to contact the skin of the human pregnant subject,
   wherein the flexible membrane is configured to transduce transmitted acoustic signals to the body; and
   wherein the body is configured to transmit the transduced acoustic signals to the microphone;
d) an electrical conductor electrically connected to the microphone; and
e) a connector in electrical contact with the electrical conductor for connection to a lead wire.

In one embodiment, body is configured to be located within a housing that attaches the microphone to a garment.

In one embodiment, the microphone is located within a structure configured to isolate the microphone from acoustic signals not from the abdomen of the pregnant human subject.

In one embodiment the body and the structure configured to isolate the microphone from acoustic signals not from the abdomen of the pregnant human subject are configured to be located within a housing that attaches the microphone to a garment.

In one embodiment, the garment is configured to be worn around the abdomen of the pregnant human subject.

In one embodiment, the garment is a belt.

In one embodiment, the present invention provides a garment, comprising:
at least one pair of acoustic sensors,
   wherein the garment is configured to arrange the individual electrodes of the at least one acoustic sensor pair to encircle the uterus of the pregnant human subject when the garment is worn, and
   wherein the individual acoustic sensor of the at least one acoustic sensor pair comprise:
   a) a body formed of a solid integral mass having a circular apron with two opposite major side walls,
      i. one side wall being concave in configuration and the other side wall having a rearwardly facing portion coaxially formed thereon, the rearwardly facing portion defining an attachment for a microphone;
      ii. an opening coaxially formed through the rearwardly facing portion; and
      iii. an annular edge connecting the periphery of the side walls;
   b) a microphone, attached to the rearwardly facing portion,
      wherein the microphone is configured to produce electrical signals in response to acoustic signals transmitted from an abdomen of a pregnant subject;
   c) a flexible membrane covering the one side wall,
      wherein the edge of the flexible membrane covers the annular edge of the one side wall,
      wherein the flexible membrane is configured to contact the skin of the human pregnant subject,
      wherein the flexible membrane is configured to transduce transmitted acoustic signals to the body; and
      wherein the body is configured to transmit the transduced acoustic signals to the microphone;
   d) an electrical conductor electrically connected to the microphone; and
   e) a connector in electrical contact with the electrical conductor for connection to a lead wire.

In one embodiment, the distance between the two side walls define a thickness, wherein the thickness has a minimum value between 1 mm to 5 mm.

In one embodiment, the concave configuration defines a cone with a height from 1 mm to 15 mm.

DETAILED DESCRIPTION

Figure 1:
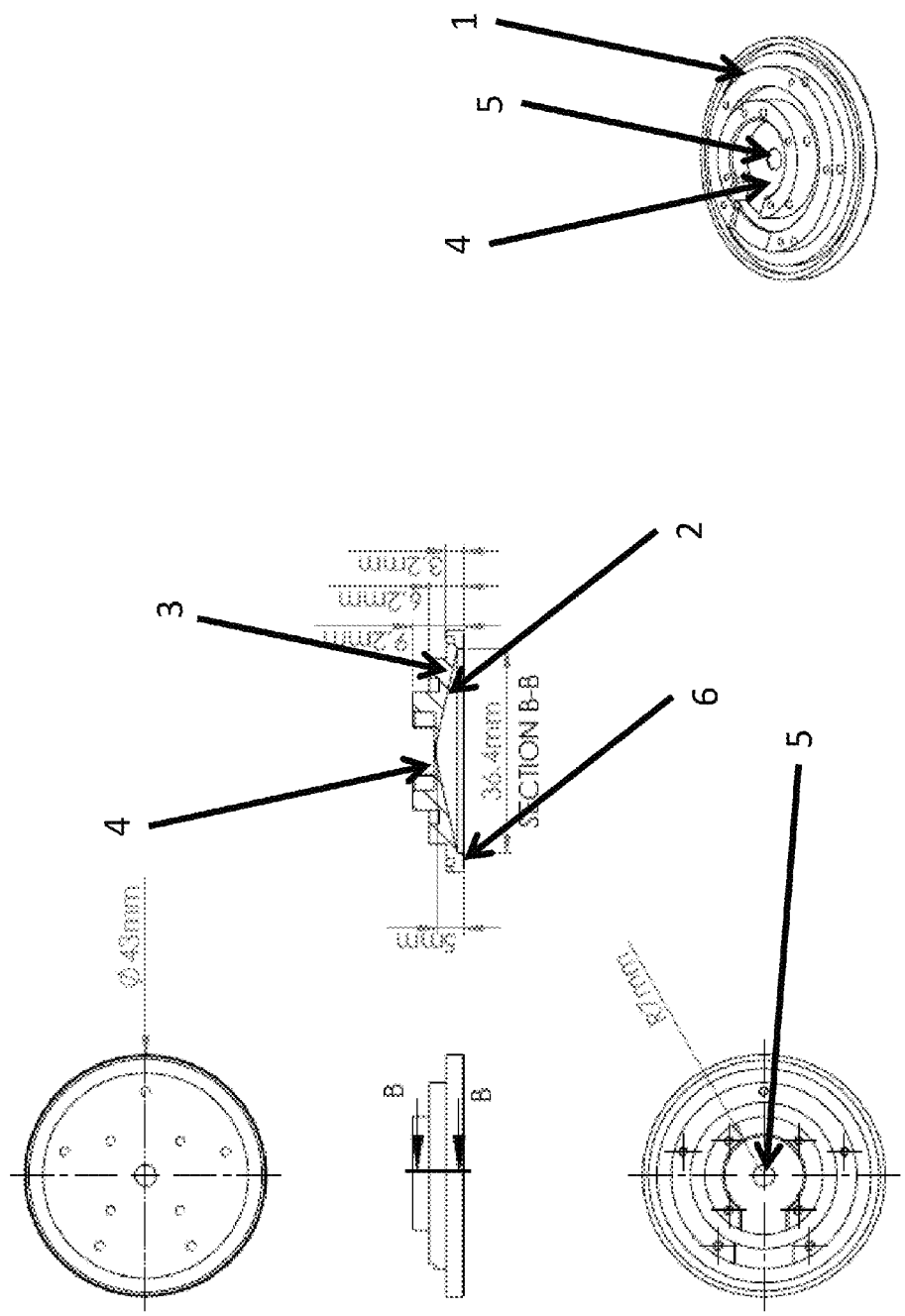
FIG. 1 shows a body of an acoustic sensor according to some embodiments of the present invention.

For clarity of disclosure, and not by way of limitation, the detailed description of the invention is divided into the following subsections that describe or illustrate certain features, embodiments or applications of the present invention.

In one embodiment, the present invention provides a garment that includes:
  a) at least one electrocardiogram sensor configured to contact the skin of the abdomen of a pregnant human subject and detect fetal and maternal cardiac electrical activity;
  b) at least one acoustic sensor configured to contact the skin of the abdomen of a pregnant human subject and detect fetal and maternal cardiac electrical activity; and
  c) a garment configured to position and contact the at least one electrocardiogram sensor and the at least one acoustic sensor on the abdomen of the pregnant human subject.

In one embodiment, the garment is further configured to include:
  d) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;
  e) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

f) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:

i. receiving a calculated fetal heart rate for a plurality of time points over a particular time interval from filtered N-ECG fetal signals data and a calculated fetal heart rate for a plurality of time points over a particular time interval from filtered PCG outputs;

ii. determining the score of the calculated fetal heart rate for the plurality of time points over the particular time interval for the filtered N-ECG fetal signals;

iii. determining the score of the calculated fetal heart rate for the plurality of time points over the particular time interval for the filtered PCG outputs;

iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval, wherein the consolidated fetal heart rate and score for an individual time point within the plurality of time points is determined as one of the four options selected from the group consisting of:

1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;

2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;

3. the calculated heart rate that has the valid score; and 4. no consolidated fetal heart rate and score, if neither the calculated heart rate from the filtered N-ECG fetal signals data or the filtered PCG outputs has a valid score;

v. based on the consolidated heart rate and scores for the plurality of time points over the particular time interval, generating, by the at least one computer processor, a fetal heart rate probability mesh;

vi. based on the fetal heart rate probability mesh, generating, by the at least one computer processor, an estimated fetal heart rate over the particular time interval, wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In some embodiments, the garment is configured to be worn around the abdomen of the pregnant human subject.

In some embodiments, the garment is a belt.

Figure 2:
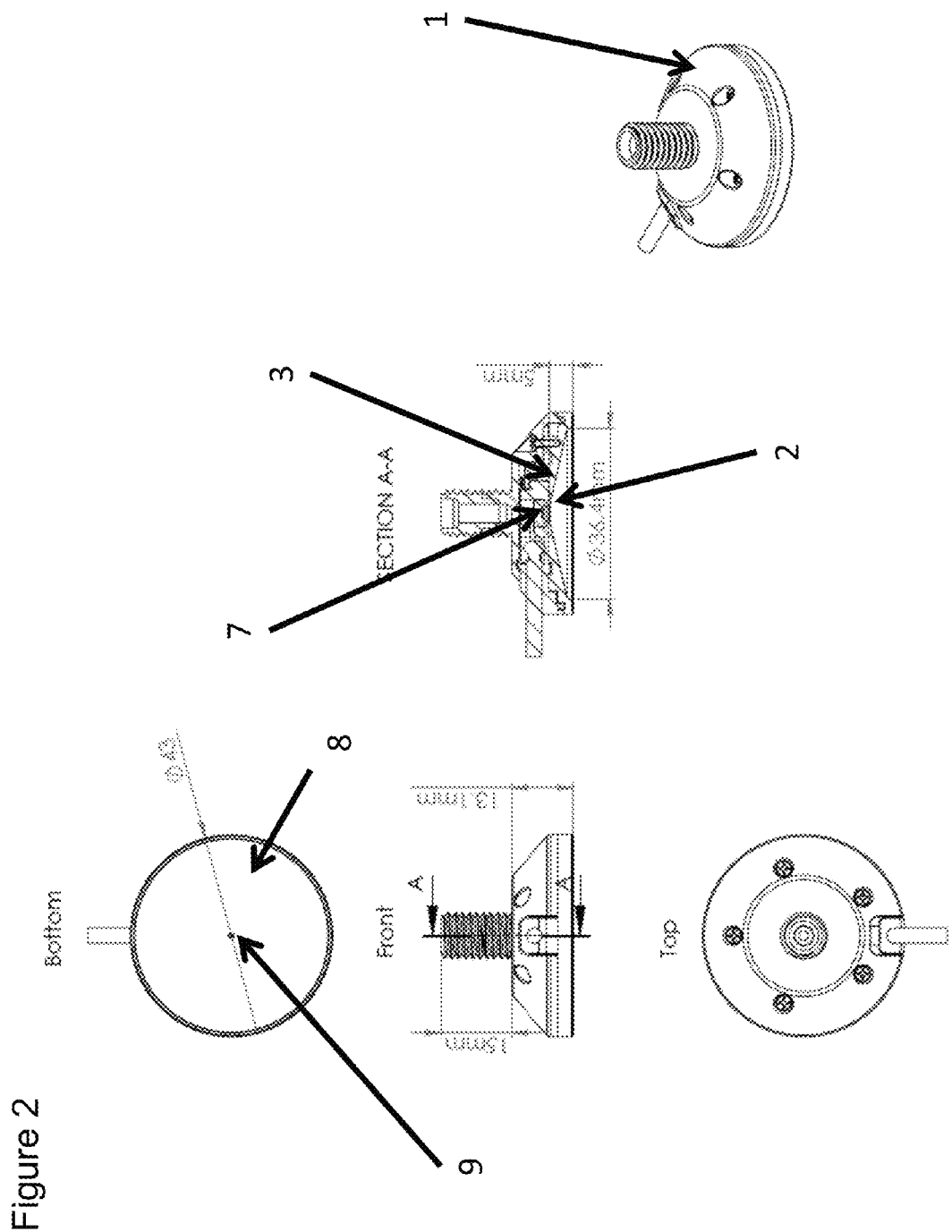
FIG. 2 shows a body of an acoustic sensor located within a housing according to some embodiments of the present invention.
Figure 3:
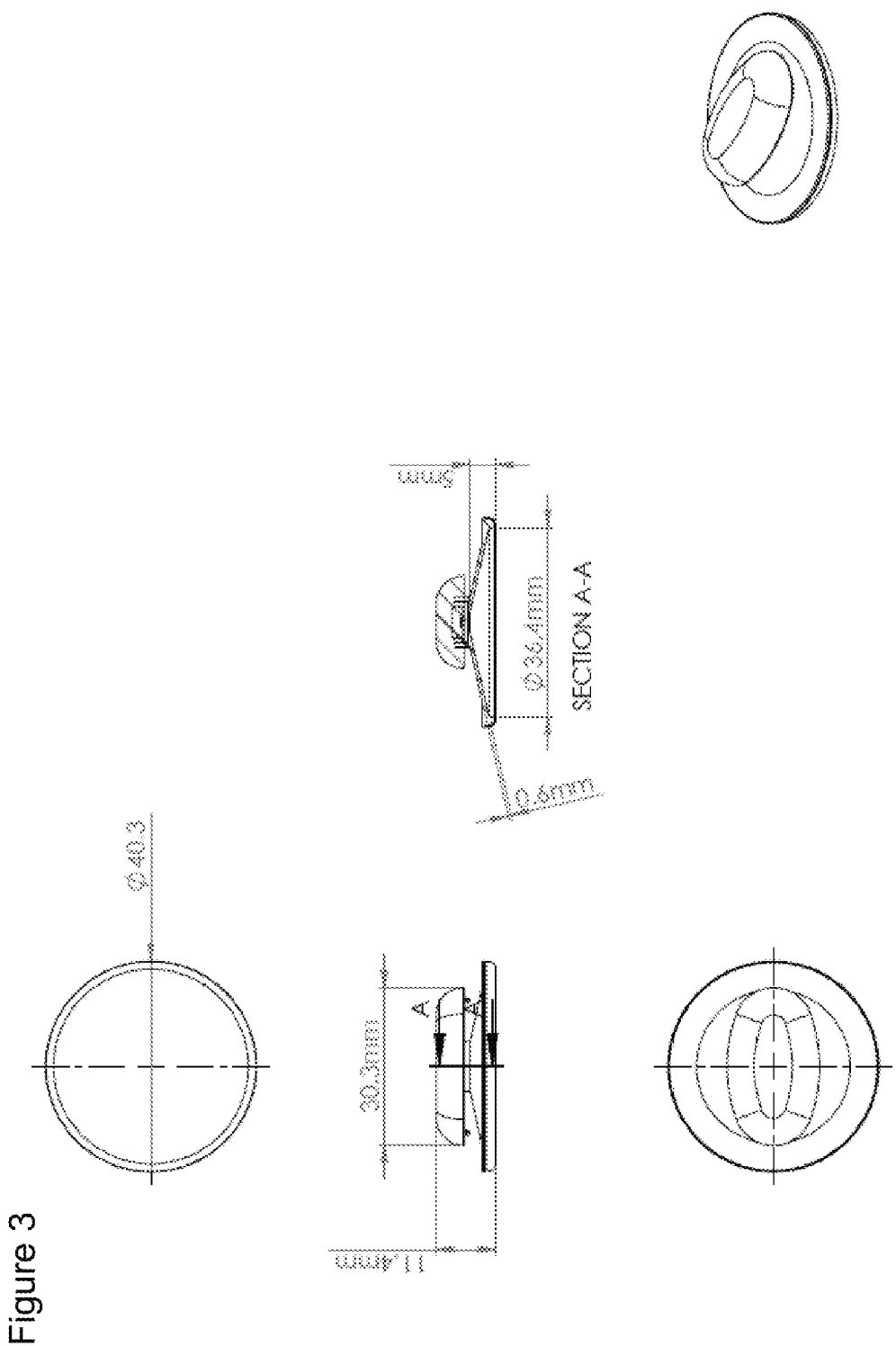
FIG. 3 shows another housing according to some embodiments of the present invention.

In some embodiments, the at least one acoustic sensor is located in the garment using the housing shown in FIG. 2. Alternatively, in some embodiments, the at least one acoustic sensor is located in the garment using the housing shown in FIG. 3.

In some embodiments, the at least one acoustic sensor is configured to compensate for the changes in sound propagation caused by the skin-air interface. Acoustic signals comprise sound waves or vibrations that propagate as a mechanical wave of pressure and displacement, through a medium such as air, water, or the body. Without intending to be limited to any particular theory, the behavior of sound propagation can be affected by the relationship between the density and pressure of the medium though which the sound wave propagates. Also, the behavior of sound propagation can be affected by the motion of the medium though which the sound wave propagates. Furthermore, the behavior of sound propagation can be affected by the viscosity of the medium though which the sound wave propagates.

Without intending to be limited to any particular theory, during a normal cardiac contraction cycle, the hear produces the following sounds: $S_1$, which corresponds to the QRS complex of the cardiac electrical activity observed during a normal cardiac contraction cycle, and is caused by the block of reverse blood flow due to closure of the tricuspid and mitral (bicuspid) valves, at the beginning of ventricular contraction, or systole. $S_2$, which corresponds to the T wave of the cardiac electrical activity observed during a normal cardiac contraction cycle, and is caused by the closure of the aortic and pulmonary valves.

Referring to FIG. 1 and FIG. 2, the at least one acoustic sensor comprises a body (1) formed of a solid integral mass having a circular apron with two opposite major side walls (2) and (3); one side wall (2) being concave in configuration and the other side wall (3) having a rearwardly facing portion (4) coaxially formed thereon, the rearwardly facing portion (4) defining an attachment for a microphone; an opening (5) coaxially formed through the rearwardly facing portion; and an annular edge (6) connecting the periphery of the side walls; a microphone (7), attached to the rearwardly facing portion (4), wherein the microphone (7) is configured to produce electrical signals in response to acoustic signals transmitted from an abdomen of a pregnant subject; a flexible membrane (8) covering the one side wall, wherein the edge of the flexible membrane (8) covers the annular edge (6) of the one side wall, wherein the flexible membrane (8) is configured to contact the skin of the human pregnant subject, wherein the flexible membrane (8) is configured to transduce transmitted acoustic signals to the body (1); and wherein the body (1) is configured to transmit the transduced acoustic signals to the microphone (7); an electrical conductor electrically connected to the microphone; and a connector in electrical contact with the electrical conductor for connection to a lead wire.

In some embodiments, the microphone (7) is lockingly engaged on the rearwardly facing portion (4) via friction. Alternative mechanisms to lockingly engage the microphone (7) on the rearwardly facing portion (4) include adhesive, screw threads, and the like.

Figure 4:
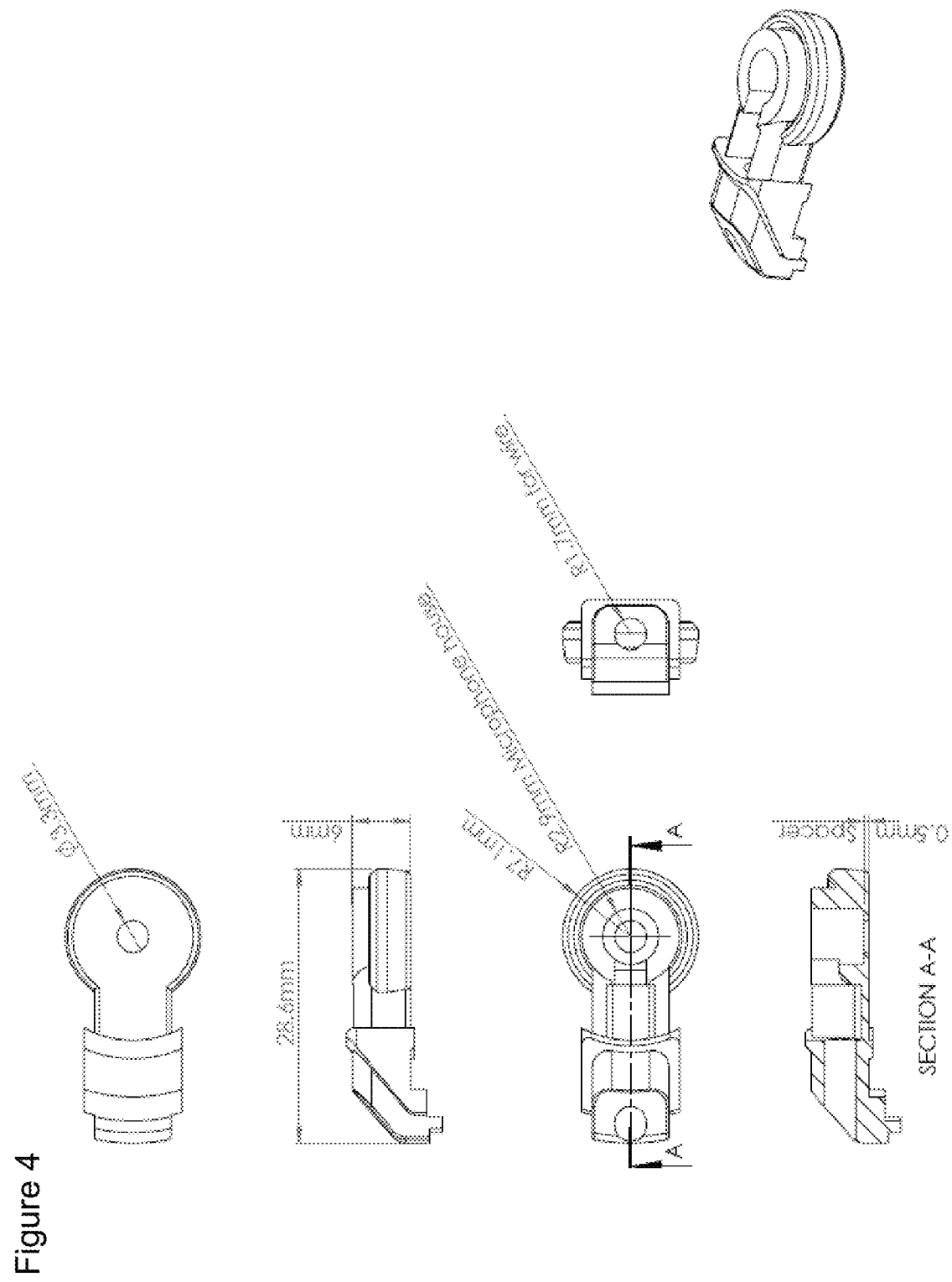
FIG. 4 shows a structure configured to isolate the microphone from acoustic signals not from the abdomen of the pregnant human subject.

Referring to FIG. 4, in some embodiments, the microphone is lockingly engaged in a structure configured to isolate the microphone (7) from acoustic signals not from the abdomen of the pregnant human subject, and position the microphone (7) on the rearwardly facing portion (4). Examples of acoustic signals not from the abdomen of the pregnant human subject include, but are not limited to sounds caused by movement of the pregnant human subject, or environmental noise.

In some embodiments, the microphone (7) is lockingly engaged in the structure configured to isolate the microphone (7) from acoustic signals not from the abdomen of the pregnant human subject by friction. Alternative mechanisms to lockingly engage the microphone (7) in the structure configured to isolate the microphone (7) from acoustic signals not from the abdomen of the pregnant human subject include adhesive, screw threads, and the like.

In the embodiment shown in FIG. 2, the flexible membrane (8) has a hole (9). Alternatively, the flexible membrane (8) lacks a hole, and the flexible membrane (8) forms an air-tight chamber, defined by the body (1) and the flexible membrane (8).

In some embodiments, the present invention provides at least one acoustic sensor configured to detect fetal cardiac activity signals, comprising:
 a) a body (1) formed of a solid integral mass having a circular apron with two opposite major side walls (2) and (3),
  i. one side wall (2) being concave in configuration and the other side wall (3) having a rearwardly facing portion (4) coaxially formed thereon, the rearwardly facing portion defining an attachment for a microphone;
  ii. an opening (5) coaxially formed through the rearwardly facing portion; and
  iii. an annular edge (6) connecting the periphery of the side walls (2) and (3);
 b) a microphone (7), attached to the rearwardly facing portion (4),
  wherein the microphone (7) is configured to produce electrical signals in response to acoustic signals transmitted from an abdomen of a pregnant subject;
 c) a flexible membrane (8) covering the one side wall, wherein the edge of the flexible membrane (8) covers the annular edge (6) of the one side wall,
  wherein the flexible membrane (8) is configured to contact the skin of the human pregnant subject,
  wherein the flexible membrane (8) is configured to transduce transmitted acoustic signals to the body (1); and
  wherein the body (1) is configured to transmit the transduced acoustic signals to the microphone (7);
 d) an electrical conductor electrically connected to the microphone; and
 e) a connector in electrical contact with the electrical conductor for connection to a lead wire.

In some embodiments, the at least one acoustic sensor is configured to reduce the acoustic impedance mismatch between skin and air, thereby improving the performance of the at least one sensor.

Without intending to be limited to any particular theory, the body (1) is configured to detect fetal cardiac activity, but isolate the microphone (7) from acoustic signals not from the abdomen of the pregnant human subject, and position the microphone (7) at the opening (5). Examples of acoustic signals not from the abdomen of the pregnant human subject include, but are not limited to sounds caused by movement of the pregnant human subject, or environmental noise. The sensitivity of the at least one acoustic sensor according to some embodiments of the present invention to fetal cardiac activity can be altered by varying one or more parameters selected from the group consisting of: the flexibility of the flexible membrane, the diameter of the body, the sensitivity of the microphone, the material of the body, the size of the body, the height of the cone defined by the concave configuration of the side wall (2), the material of the isolation structure, and the algorithm used to extract fetal cardiac activity data from acoustic signals.

Figure 5:
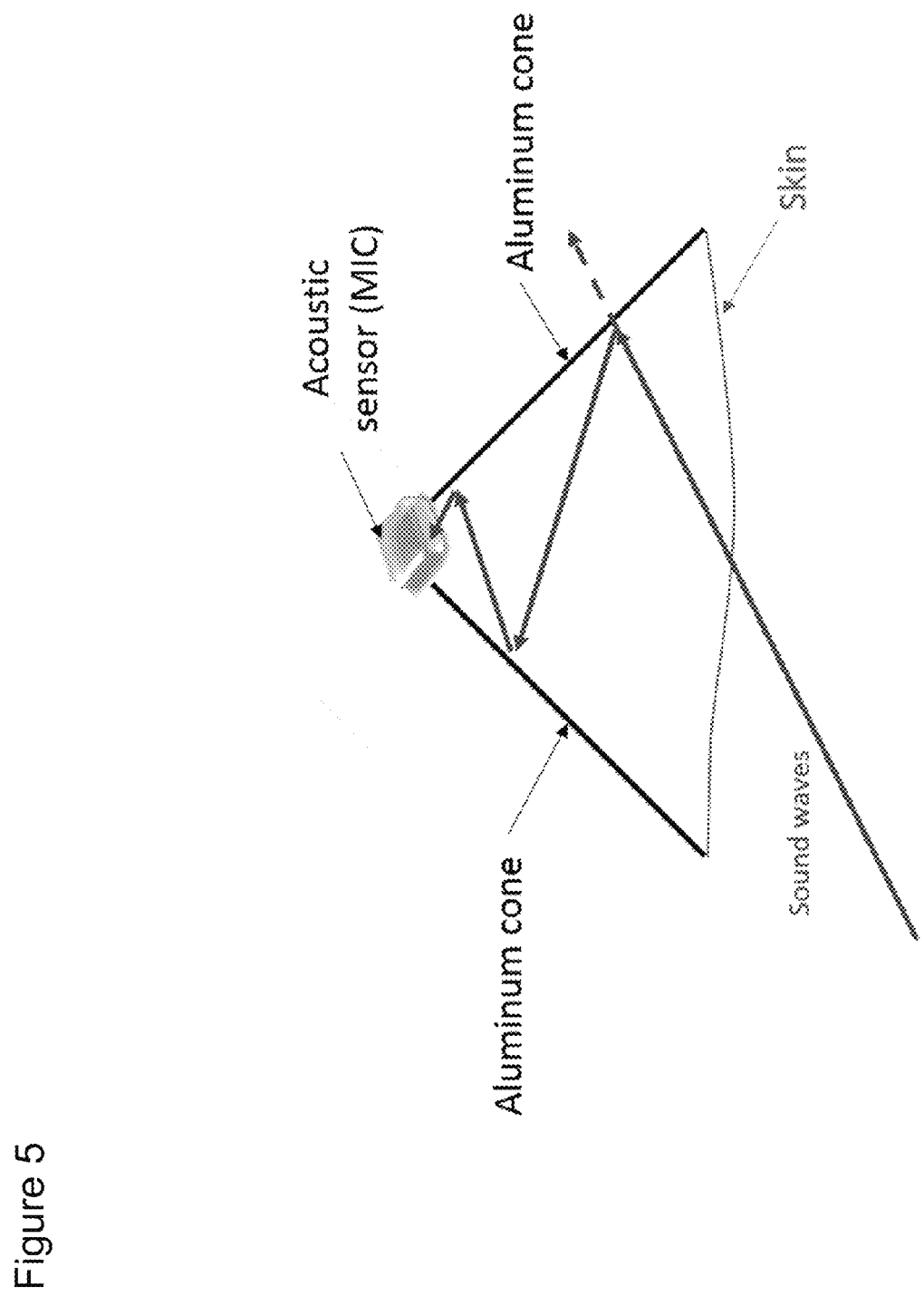
FIG. 5 shows a representation of the transduction of acoustic signals using an acoustic sensor according to some embodiments of the present invention.

For example, by way of illustration, a larger acoustic sensor would be able collect more acoustic signals than a smaller one. By way of another illustration, an aluminum body would reflect sound waves more efficiently (see, for example FIG. 5 than a plastic body.)

In some embodiments, the body (1) is circular, with an outer diameter configured to detect fetal cardiac activity. In some embodiments, the body (1) is circular, with an outer diameter of 20 mm to 60 mm. In some embodiments, body (1) is circular, with an outer diameter of 60 mm. In some embodiments, body (1) is circular, with an outer diameter of 50 mm. In some embodiments, body (1) is circular, with an outer diameter of 43 mm. In some embodiments, body (1) is circular, with an outer diameter of 40 mm. In some embodiments, body (1) is circular, with an outer diameter of 30 mm. In some embodiments, housing is body (1), with an outer diameter of 20 mm.

In some embodiments, the body (1) is non-circular in shape. Examples of non-circular shapes suitable for use according to some embodiments of the present invention include, but are not limited to, oval, square, rectangular, and the like.

In one embodiment, the distance between the two side walls (2) and (3) defines a thickness, wherein the thickness has a minimum value between 0.3 mm to 5 mm. In some embodiments, the thickness is configured to detect fetal cardiac activity. In some embodiments, the thickness is 5 mm. Alternatively, the thickness is 4 mm. Alternatively, the thickness is 3 mm. Alternatively, the thickness is 2 mm. Alternatively, the thickness is 1 mm. Alternatively, the thickness is 0.9 mm. Alternatively, the thickness is 0.8 mm. Alternatively, the thickness is 0.7 mm. Alternatively, the thickness is 0.6 mm. Alternatively, the thickness is 0.5 mm. Alternatively, the thickness is 0.4 mm. Alternatively, the thickness is 0.3 mm.

In some embodiments, the concave configuration of the side wall (2) defines a cone with a height from 1 mm to 15 mm. In some embodiments, the height of the cone is configured to detect fetal cardiac activity. In some embodiments, the height of the cone is 15 mm. Alternatively, in some embodiments, the height of the cone is 14 mm. Alternatively, in some embodiments, the height of the cone is 13 mm. Alternatively, in some embodiments, the height of the cone is 12 mm. Alternatively, in some embodiments, the height of the cone is 11 mm. Alternatively, in some embodiments, the height of the cone is 10 mm. Alternatively, in some embodiments, the height of the cone is 9 mm. Alternatively, in some embodiments, the height of the cone is 8 mm. Alternatively, in some embodiments, the height of the cone is 7 mm. Alternatively, in some embodiments, the height of the cone is 6 mm. Alternatively, in some embodiments, the height of the cone is 5 mm. Alternatively, in some embodiments, the height of the cone is 4 mm. Alternatively, in some embodiments, the height of the cone is 3 mm. Alternatively, in some embodiments, the height of the cone is 2 mm. Alternatively, in some embodiments, the height of the cone is 1 mm.

In some embodiments, the height of the cone is less than or equal to ¼ the diameter of the base of the body (1).

In some embodiments, the body (1) is configured to have an acoustic gain of 50 dB. Alternatively, in some embodiments, the body (1) is configured to have an acoustic gain of 40 dB. Alternatively, in some embodiments, the body (1) is configured to have an acoustic gain of 30 dB. Alternatively, in some embodiments, the body (1) is configured to have an acoustic gain of 20 dB. Alternatively, in some embodiments, the body (1) is configured to have an acoustic gain of 10 dB.

In some embodiments, the acoustic gain is greater than the loss in transmission of the acoustic signal between skin and air as a result of the equivalent acoustic impedance mismatch.

In some embodiments, the loss in transmission is calculated using the equation:

$$\tau = 4 \frac{Z_{air} * Z_{skin}}{(Z_{air} + Z_{skin})^2}$$
$$\rightarrow \tau \cong -29 \text{ dB}$$

Where:
$Z_{air}$ is the equivalent acoustic impedance of air
$Z_{skin}$ is the equivalent acoustic impedance of skin In some embodiments, the minimum acoustic gain $G_{min}$ required to compensate the loss $\tau$ is approximated using the equation:

$$\propto \frac{A_{base}}{A_{hole}} = \left(\frac{D_{base}}{D_{hole}}\right)^2 = \left(\frac{R_{base}}{r_{hole}}\right)^2$$

$$G_{min} = 29 \text{ dB} = 10 \log10\left(\left(\frac{R_{base}}{r_{hole}}\right)^2\right) = 20 \log10\left(\frac{R_{base}}{r_{hole}}\right)$$

$$\rightarrow \frac{R_{base}}{r_{hole}} \geq 10^{\frac{29}{20}} = 28$$

Where:
$A_{base}$ is the space of the base
$A_{hole}$ is the space of the hole
$R_{base}$ is the radius of the base
$r_{hole}$ is the radius of the hole
$D_{base}$ is the diameter of the base
$D_{hole}$ is the diameter of the hole In some embodiments, the hole (5) has a diameter from 2 mm to 5 mm. In some embodiments, the hole (5) has a diameter of 5 mm. In some embodiments, the hole (5) has a diameter of 4 mm. In some embodiments, the hole (5) has a diameter of 3 mm. In some embodiments, the hole (5) has a diameter of 2 mm.

Referring to FIG. 4, in some embodiments, microphone (7) is lockingly engaged within a structure configured to isolate the microphone (7) from acoustic signals not from the abdomen of the pregnant human subject, and wherein the structure is configured to locate the microphone over the hole (5). In some embodiments, the structure is has a spacer from 0.2 to 2 mm. In some embodiments, the spacer is 2 mm. In some embodiments, the spacer is 1.9 mm. In some embodiments, the spacer is 1.8 mm. In some embodiments, the spacer is 1.7 mm. In some embodiments, the spacer is 1.6 mm. In some embodiments, the spacer is 1.5 mm. In some embodiments, the spacer is 1.4 mm. In some embodiments, the spacer is 1.3 mm. In some embodiments, the spacer is 1.2 mm. In some embodiments, the spacer is 1.1 mm. In some embodiments, the spacer is 1.0 mm. In some embodiments, the spacer is 0.9 mm. In some embodiments, the spacer is 0.8 mm. In some embodiments, the spacer is 0.7 mm. In some embodiments, the spacer is 0.6 mm. In some embodiments, the spacer is 0.5 mm. In some embodiments, the spacer is 0.4 mm. In some embodiments, the spacer is 0.3 mm. In some embodiments, the spacer is 0.2 mm.

In some embodiments, the structure has a hole that transmits the acoustic signals from the body to the microphone (7). In some embodiments the structure is configured to lockingly engage the microphone (7). In some embodiments, the microphone is lockingly engaged within the structure via an adhesive.

In some embodiments, the structure has a height configured to isolate the microphone (7) from acoustic signals not from the abdomen of the pregnant human subject. In some embodiments, the height is from 0.4 mm to 9 mm. In some embodiments, the height is 9 mm. In some embodiments, the height is 8 mm. In some embodiments, the height is 7 mm. In some embodiments, the height is 6 mm. In some embodiments, the height is 5.5 mm. In some embodiments, the height is 5 mm. In some embodiments, the height is 4.5 mm. In some embodiments, the height is 4 mm. In some embodiments, the height is 3.5 mm. In some embodiments, the height is 3 mm. In some embodiments, the height is 2.5 mm. In some embodiments, the height is 2 mm. In some embodiments, the height is 1.5 mm. In some embodiments, the height is 1 mm. In some embodiments, the height is 0.9 mm. In some embodiments, the height is 0.8 mm. In some embodiments, the height is 0.7 mm. In some embodiments, the height is 0.6 mm. In some embodiments, the height is 0.5 mm. In some embodiments, the height is 0.4 mm.

In some embodiments, the structure comprises a circular portion. In some embodiments, the circular portion is configured to lockingly engage with the rearwardly facing portion (4).

In some embodiments, the circular portion has an outer diameter configured to isolate the microphone (7) from acoustic signals not from the abdomen of the pregnant human subject. In some embodiments, the outer diameter is from 6 mm to 16 mm. In some embodiments, the outer diameter is 16 mm. In some embodiments, the outer diameter is 15 mm. In some embodiments, the outer diameter is 14 mm. In some embodiments, the outer diameter is 13 mm. In some embodiments, the outer diameter is 12 mm. In some embodiments, the outer diameter is 11 mm. In some embodiments, the outer diameter is 10 mm. In some embodiments, the outer diameter is 9 mm. In some embodiments, the outer diameter is 8 mm. In some embodiments, the outer diameter is 7.1 mm. In some embodiments, the outer diameter is 7 mm. In some embodiments, the outer diameter is 6 mm.

In some embodiments the circular portion has an inner diameter configured to house the microphone (7) and isolate the microphone from acoustic signals not from the abdomen of the pregnant human subject. In some embodiments, the inner diameter is from 4 mm to 8 mm. In some embodiments, the inner diameter is 8 mm. In some embodiments, the inner diameter is 7 mm. In some embodiments, the inner diameter is 6 mm. In some embodiments, the inner diameter is 5 mm. In some embodiments, the inner diameter is 4 mm.

In some embodiments, the body (1) is made from a material configured to detect fetal cardiac activity. In some embodiments, the body (1) is made from aluminum. In alternate embodiments, the body (1) is made from brass. In alternate embodiments, the body (1) is made from stainless steel. In alternate embodiments, the body (1) is made from plastic. In some embodiments, the plastic is nylon.

In some embodiments, the structure is made from a material configured to isolate the microphone (7) from acoustic signals not from the abdomen of the pregnant human subject. In some embodiments, the structure is made from Polyurethane 60 shore. In some embodiments, the structure is a resin. Examples of materials suitable for forming the structure include, but are not limited to rubber, Silicone, TPE, TPU, and the like. In some embodiments the Polyurethane's elasticity is from 20 to 80 shore.

In some embodiments, the flexible membrane (8) is attached to the body (1) by adhesive. Alternatively, in some embodiments, the flexible membrane (8) is attached to the body (1) by crimping a portion of the flexible membrane between the body (1) and a housing, by vacuum forming, followed by snapping.

As used herein, the term "flexible" refers to the property of a membrane to deform, both to conform to the skin of the pregnant human subject, but also to transduce acoustic signals with sufficient fidelity to the microphone.

In some embodiments, the size of the flexible membrane (8), the material comprising the flexible membrane (8), the thickness of the flexible membrane (8), or any combination thereof can alter the ability of the flexible membrane (8) to contact the skin of a human pregnant subject and to transduce the acoustic signals. In some embodiments, the flexible membrane (8) is configured to contact the skin of a human pregnant subject and to transduce the acoustic signals. In some embodiments, the flexible membrane (8) is further configured to comprise a hole (9).

In some embodiments, the thickness of the flexible membrane (8) is from 0.2 mm to 0.6 mm. In some embodiments, the thickness of the flexible membrane (8) is 0.6 mm. In some embodiments, the thickness of the flexible membrane (8) is 0.5 mm. In some embodiments, the thickness of the flexible membrane (8) is 0.4 mm. In some embodiments, the thickness of the flexible membrane (8) is 0.3 mm. In some embodiments, the thickness of the flexible membrane (8) is 0.2 mm.

In some embodiments, the density of the flexible membrane (8) is 900 kg/m$^3$ to 1900 kg/m$^3$. In some embodiments, the density of the flexible membrane (8) is 1900 kg/m$^3$. In some embodiments, the density of the flexible membrane (8) is 1800 kg/m$^3$. In some embodiments, the density of the flexible membrane (8) is 1700 kg/m$^3$. In some embodiments, the density of the flexible membrane (8) is 1600 kg/m$^3$. In some embodiments, the density of the flexible membrane (8) is 1500 kg/m$^3$. In some embodiments, the density of the flexible membrane (8) is 1400 kg/m$^3$. In some embodiments, the density of the flexible membrane (8) is 1300 kg/m$^3$. In some embodiments, the density of the flexible membrane (8) is 1200 kg/m$^3$. In some embodiments, the density of the flexible membrane (8) is 1100 kg/m$^3$. In some embodiments, the density of the flexible membrane (8) is 1000 kg/m$^3$. In some embodiments, the density of the flexible membrane (8) is 900 kg/m$^3$.

In some embodiments, the flexible membrane (8) is circular, and has a diameter equal to the body. In some embodiments, the flexible membrane has same outer perimeter as the body (1).

In some embodiments, the flexible membrane (8) is circular, and has a diameter from 20 mm to 50 mm. In some embodiments, the flexible membrane (8) is circular, and has a diameter of 50 mm. In some embodiments, the flexible membrane (8) is circular, and has a diameter of 44 mm. In some embodiments, the flexible membrane (8) is circular, and has a diameter of 40 mm. In some embodiments, the flexible membrane (8) is circular, and has a diameter of 38 mm. In some embodiments, the flexible membrane (8) is circular, and has a diameter of 36 mm. In some embodiments, the flexible membrane (8) is circular, and has a diameter of 34 mm. In some embodiments, the flexible membrane (8) is circular, and has a diameter of 30 mm. In some embodiments, the flexible membrane (8) is circular, and has a diameter of 26 mm. In some embodiments, the flexible membrane (8) is circular, and has a diameter of 20 mm.

In some embodiments, the hole (9) has a diameter ranging from 0.4 mm to 1.2 mm. In some embodiments, the hole (9) has a diameter of 1 mm. In some embodiments, the hole (9) has a diameter of 0.8 mm. In some embodiments, the hole (9) has a diameter of 0.6 mm. In some embodiments, the hole (9) has a diameter of 0.4 mm. In some embodiments, the hole (9) is absent.

In some embodiments, the flexible membrane comprises PVC. In some embodiments the flexible membrane comprises Polyester, Polycarbonate. In some embodiments, the flexible membrane comprises a Phenoxy resin. In some embodiments, the flexible membrane comprises BoPET, such as, for example, the membrane sold under the trade name MYLAR®. In some embodiments, the flexible membrane comprises BoPET, such as, for example, the membrane sold under the trade name HOSTAPHAN®.

In some embodiments, the flexible membrane is the flexible membrane disclosed in U.S. Pat. No. 3,276,536.

In some embodiments, the microphone (7) is configured to detect fetal cardiac activity.

In some embodiments, the microphone (7) is a free air microphone. Alternatively, in some embodiments, the microphone (7) is a contact microphone. Alternatively, in some embodiments, the microphone (7) is a hybrid free air and contact microphone.

In some embodiments, the microphone (7) is configured to detect sub-ELF (extremely low frequency) signals. In some embodiments, the microphone is configured to have a flat response in the 5-150 Hz region.

In some embodiments, the microphone (7) is an electrostatic capacitor-based microphone. In some embodiments, the electrostatic capacitor-based microphone is a foil, or diaphragm type electrostatic capacitor-based microphone. In some embodiments, the electrostatic capacitor-based microphone is a back electret type electrostatic capacitor-based microphone. In some embodiments, the electrostatic capacitor-based microphone is a front electret type electrostatic capacitor-based microphone.

Figure 6:
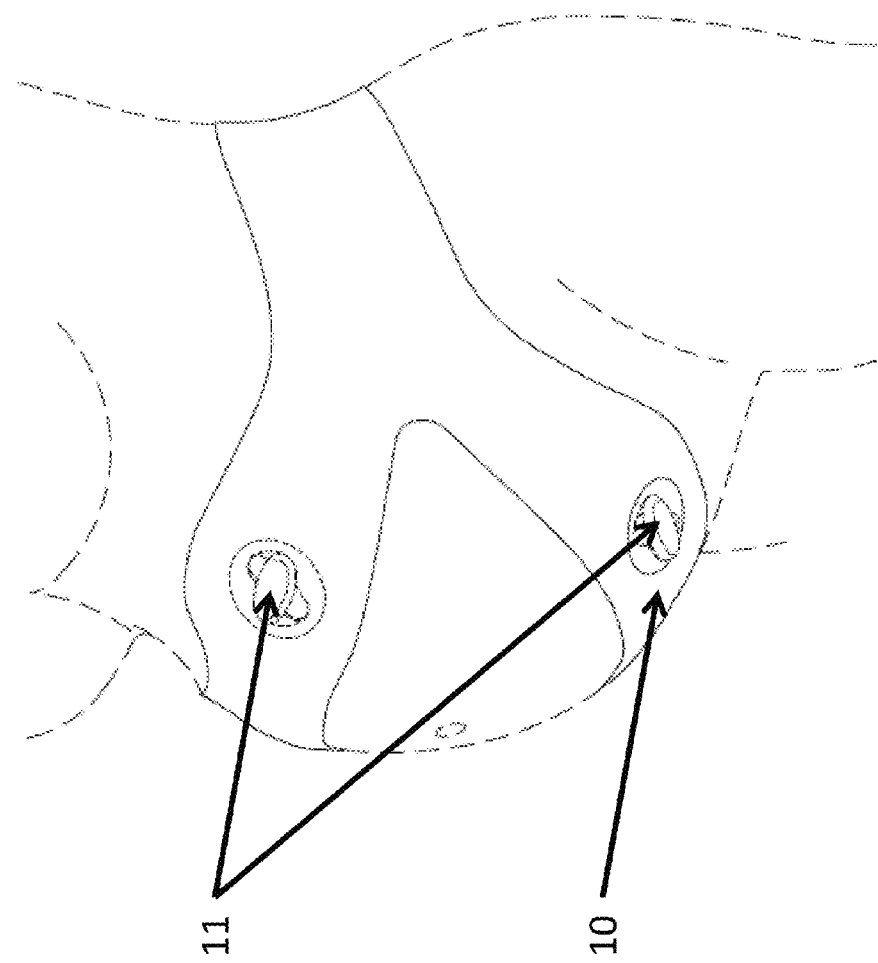
FIG. 6 shows a first view of a garment according to some embodiments of the present invention being worn by a pregnant human subject.
Figure 7:
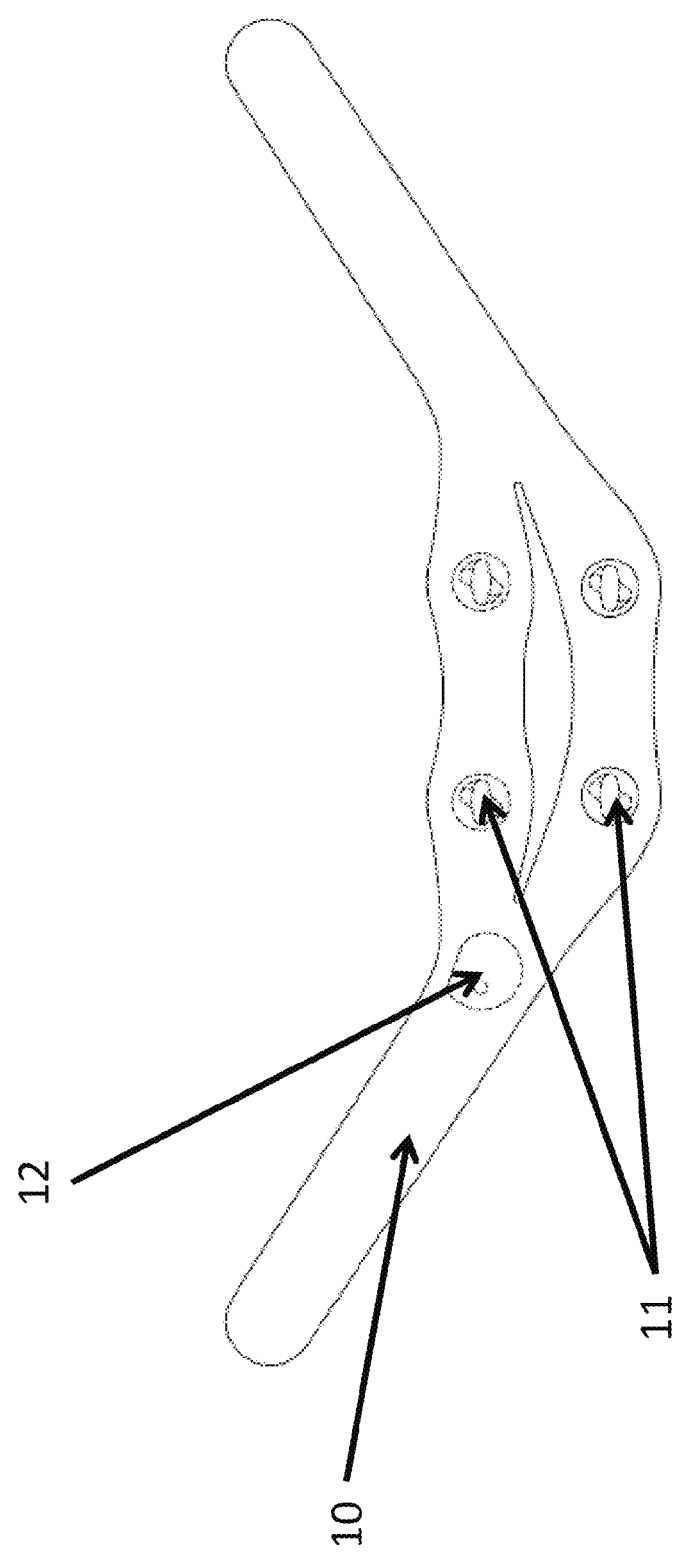
FIG. 7 shows a front view of a garment according to some embodiments of the present invention.
Figure 8:
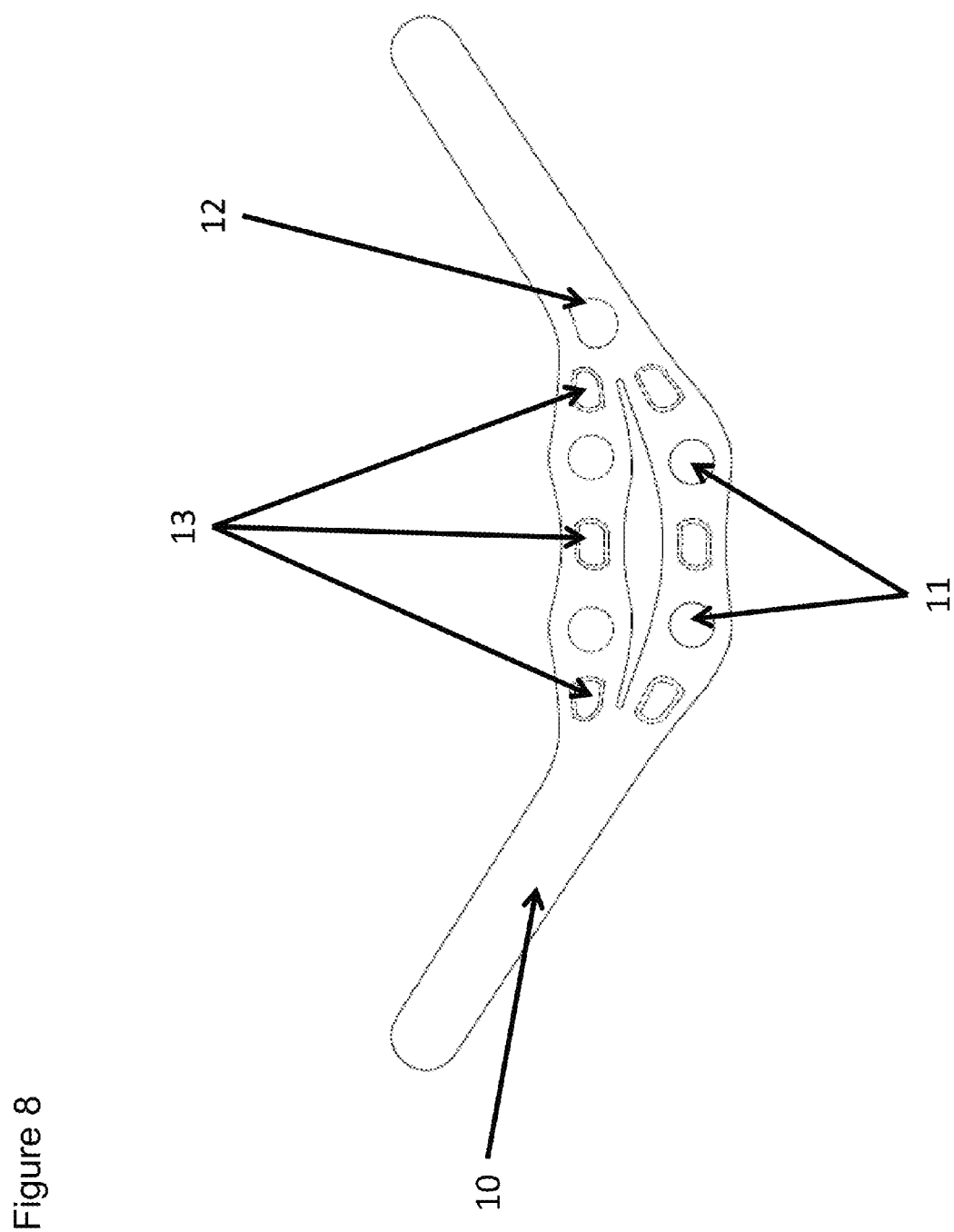
FIG. 8 shows a rear view of a garment according to some embodiments of the present invention.

Referring to FIGS. 6 to 8, an example of a garment according to some embodiments of the present invention is shown. In the embodiment shown, 4 acoustic sensors (11) are incorporated into a belt (10), wherein the belt, when worn, positions the acoustic sensors on the abdomen of the pregnant mother, such that the acoustic sensors contact the skin of the abdomen of the pregnant mother, and the acoustic sensors are positioned in a circumferential arrangement around the uterus. In the embodiments shown, the belt also contains additional sensors (13) and a transmitter (12).

In some embodiments, the additional sensors are ECG sensors.

Figure 9:
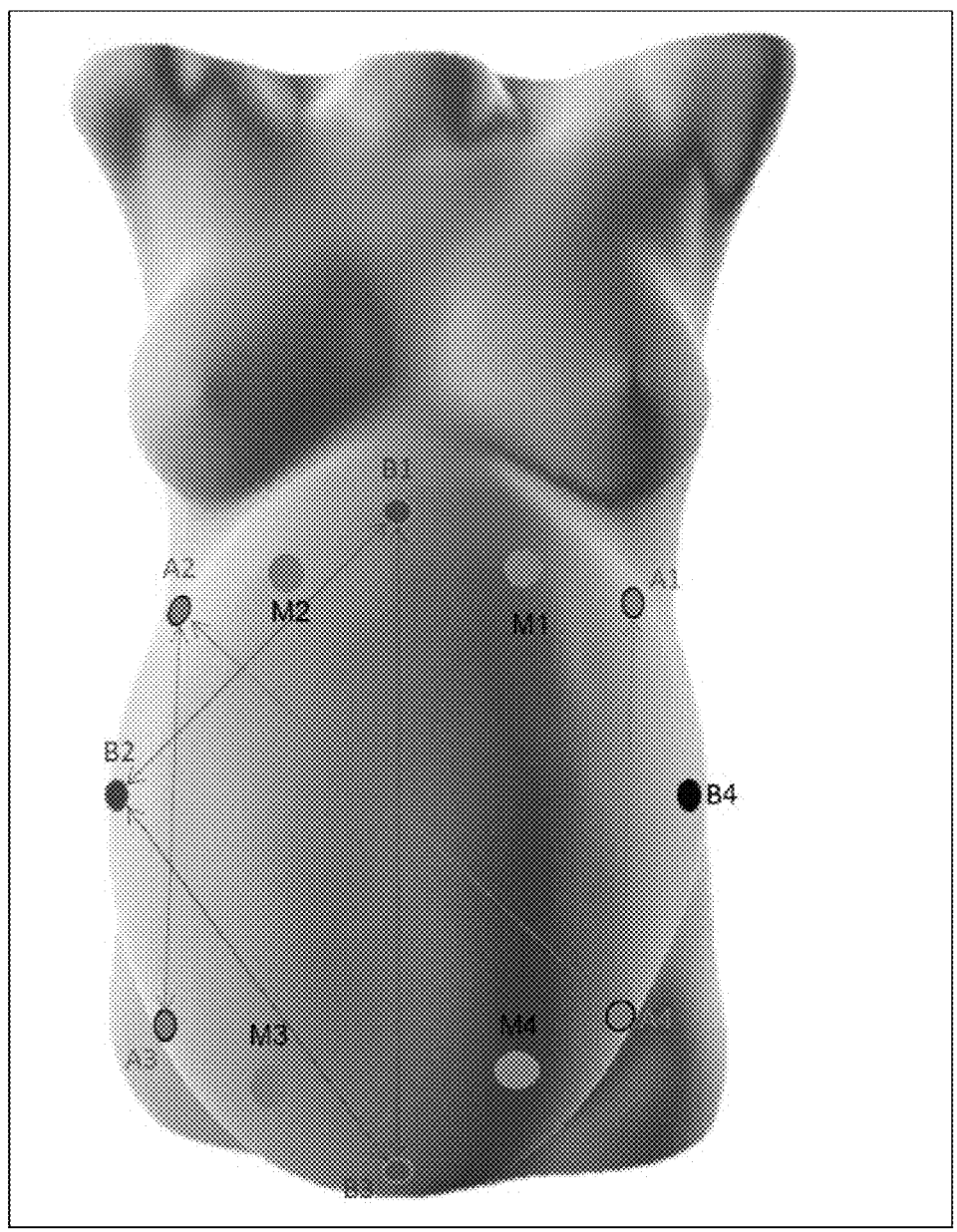
FIG. 9 shows the positions of the acoustic sensor (positions M1, M2, M3 M4) on the abdomen of the pregnant human subject according to some embodiments of the present invention.

For example, as shown in FIG. 9, the exemplary inventive system of the present invention utilizes a set of four acoustic sensors (M1-M4) at respective exemplary positions. In some embodiments, the positioning of acoustic sensors can varies based, at least in part, on, for example, shape of mother's stomach, the stage of the pregnancy, physiological characteristics of the pregnant human subject and/or fetus(es), previous acoustic and/or other types of cardio recordings (e.g., Electrocardiogram (ECG) signal recordings and analysis, etc.), and other similarly suitable data.

Figure 10:
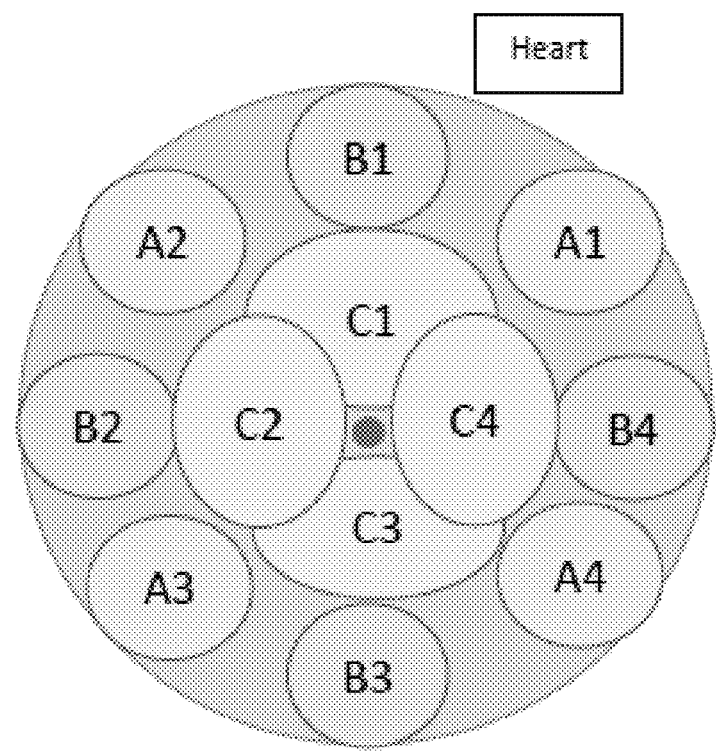
FIG. 10 shows the positions of the acoustic sensor (positions A1, A2, A3, A4, B1, B2, B3, B4, C1, C2, C3, C4) on the abdomen of the pregnant human subject according to some embodiments of the present invention.

An alternate positioning of the acoustic sensors is shown in FIG. 10.

In some embodiments, the acoustic sensors of the present invention record the internal sound produced inside the pregnant human subject with added noise from the environment. As detailed below, from these recordings the heartbeat sound of the fetus(es) and/or the pregnant human subject are extracted and the heart rate of each subject is calculated.

Figure 11:
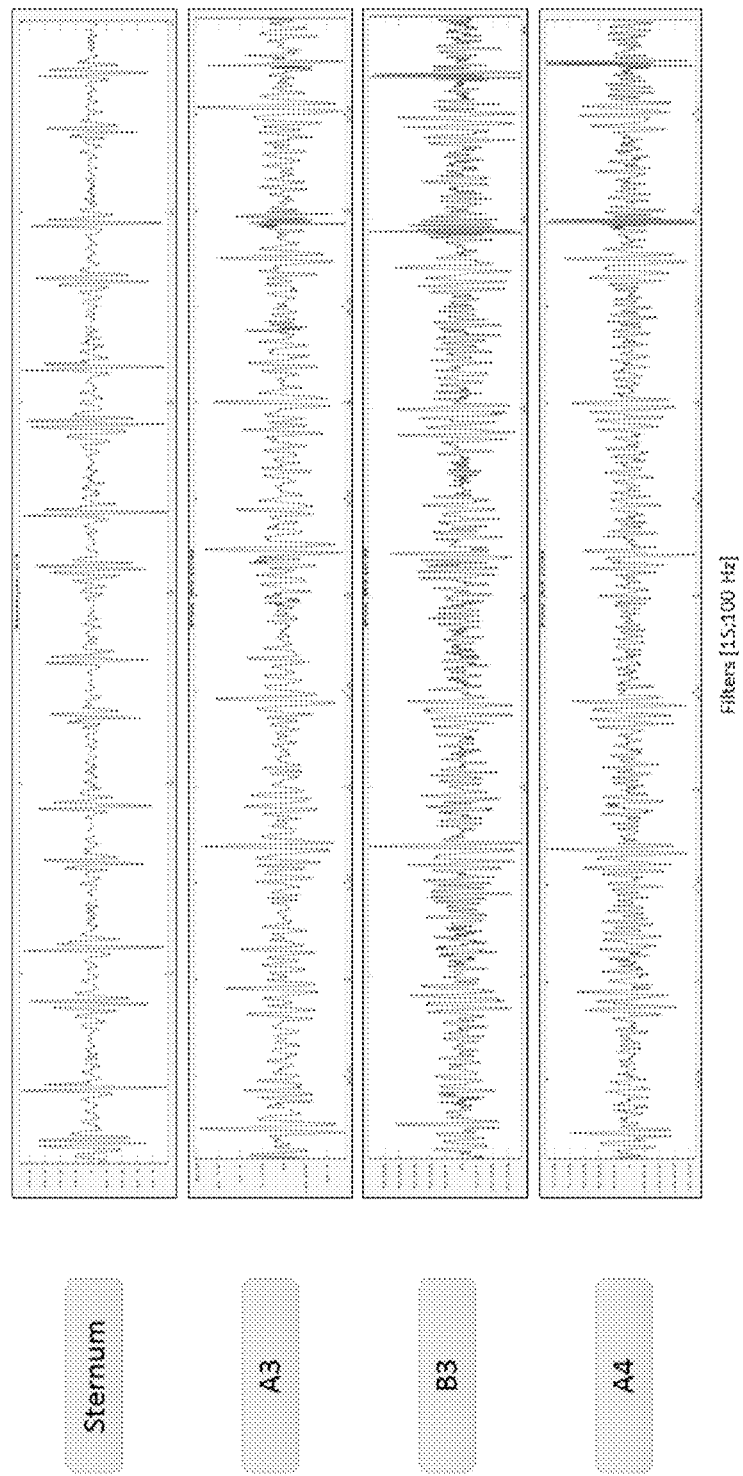
FIG. 11 shows maternal acoustic signals data received using an acoustic sensor according to some embodiments of the present invention.

In some embodiments, the level of detection by each acoustic sensor is independent of the other acoustic sensors (e.g, in FIG. 9, on other three acoustic sensors). Referring to FIG. 9, in some embodiments, it is determined that, typically, the fetal PCG signals are detected by the acoustic sensors in locations M3 and/or M4, while the maternal PCG signals are detected by the acoustic sensors in locations M1 and/or M2. In some embodiments, the maternal PCG signals can be detected by all four sensors (M1-M4) and have to be cleaned in order to detect the fetal heartbeats. In some embodiments, as detailed below, the cleaning process is performed using at least one Independent component analysis (ICA) algorithm of the present invention. For instance, in some embodiments, the inventive system of the present invention assumes that the interfering noises are audio sources which are not the fetal origin that thus are statistically independent from the fetal heart sounds. An example of maternal acoustic signals detected using an acoustic sensor according to some embodiments of the present invention is shown in FIG. 11.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An acoustic sensor consisting of:
 a) a body formed of a solid integral mass having a circular apron with two opposite major side walls,
  i. one side wall being concave in configuration and the other side wall having a rearwardly facing portion coaxially formed thereon, the rearwardly facing portion defining an attachment for a microphone;
  ii. an opening coaxially formed through the rearwardly facing portion; and
  iii. an annular edge connecting the periphery of the side walls;
 b) a microphone, attached to the rearwardly facing portion,
  wherein the microphone is configured to produce electrical signals in response to acoustic signals transmitted from an abdomen of a pregnant subject,
  wherein the microphone is located within a structure configured to isolate the microphone from acoustic signals not from the abdomen of the pregnant human subject,
  wherein the structure is configured to locate the microphone over the opening coaxially formed through the rearwardly facing portion;
 c) a flexible membrane covering the one side wall, wherein the edge of the flexible membrane covers the annular edge of the one side wall,
  wherein the flexible membrane is configured to contact the skin of the human pregnant subject,
  wherein the flexible membrane is configured to transduce transmitted acoustic signals to the body; and
  wherein the body is configured to transmit the transduced acoustic signals to the microphone;
 d) an electrical conductor electrically connected to the microphone; and
 e) a connector in electrical contact with the electrical conductor for connection to a lead wire.

2. The acoustic sensor of claim 1, wherein the body is configured to be located within a within a housing that attaches the acoustic sensor to a garment.

3. The acoustic sensor of claim 2, wherein the garment is configured to be worn around the abdomen of the pregnant human subject.

4. The acoustic sensor of claim 2, wherein the garment is a belt.

5. The acoustic sensor of claim 1, wherein the body and the structure configured to isolate the microphone from acoustic signals not from the abdomen of the pregnant human subject are configured to be located within a housing that attaches the microphone to a garment.

6. The acoustic sensor of claim 5, wherein the garment is configured to be worn around the abdomen of the pregnant human subject.

7. The acoustic sensor of claim 5, wherein the garment is a belt.

8. The acoustic sensor of claim 1, wherein the body has an outer diameter of 20 mm to 60 mm.

9. The acoustic sensor of claim 1, wherein the concave configuration defines a cone with a height from 1 mm to 15 mm.

* * * * *